(12) United States Patent
Festag et al.

(10) Patent No.: US 6,258,081 B1
(45) Date of Patent: Jul. 10, 2001

(54) ARRANGEMENT FOR LASER COAGULATION

(75) Inventors: Karsten Festag, Jena; Peter Wengler, Erfurt, both of (DE)

(73) Assignee: Asclepion-Meditec AG, Jena (DE)

( * ) Notice: Subject to any disclaimer, the term of this patent is extended or adjusted under 35 U.S.C. 154(b) by 0 days.

(21) Appl. No.: 09/131,852

(22) Filed: Aug. 7, 1998

(30) Foreign Application Priority Data

Aug. 11, 1997 (DE) .............................. 197 34 655

(51) Int. Cl.$^7$ ...................................... A61B 18/18
(52) U.S. Cl. .................. 606/4; 606/10; 351/213
(58) Field of Search ............... 606/4–6, 10, 11, 606/17, 18; 351/205, 211, 213, 214, 215, 221

(56) References Cited

U.S. PATENT DOCUMENTS

| | | | |
|---|---|---|---|
| 3,796,220 | * | 3/1974 | Bredemeier ............... 606/18 |
| 5,311,224 | * | 5/1994 | Enomoto .................. 606/4 |
| 5,425,729 | * | 6/1995 | Ishida et al. ............. 606/4 |
| 5,634,923 | * | 6/1997 | Brenner et al. ........... 606/10 |

FOREIGN PATENT DOCUMENTS

| | | |
|---|---|---|
| 7925899 U1 | 9/1979 | (DE) . |
| WO 87/05495 | 3/1987 | (WO) . |

* cited by examiner

*Primary Examiner*—Michael Peffley
(74) *Attorney, Agent, or Firm*—Reed Smith LLP

(57) ABSTRACT

An arrangement for laser coagulation at the ocular fundus with at least one illumination light source for an illumination beam path, with a laser arrangement for generating a sighting and therapy beam path, wherein the sighting radiation and therapy radiation have different wavelengths, with observation optics for visual observation of the ocular fundus, for selecting the coagulation site and/or for monitoring the results of coagulation, and with a protective mechanism which prevents the laser radiation from penetrating into the eye of the person administering treatment. An optical element arranged in the sighting and therapy beam path is provided as a protective device, wherein this optical element has a plurality of optically active areas whose optical characteristics differ from one another. In this way, an uncomplicated construction of the device which is characterized by an extremely high degree of safety for the treating person is achieved.

8 Claims, 2 Drawing Sheets

Section AA

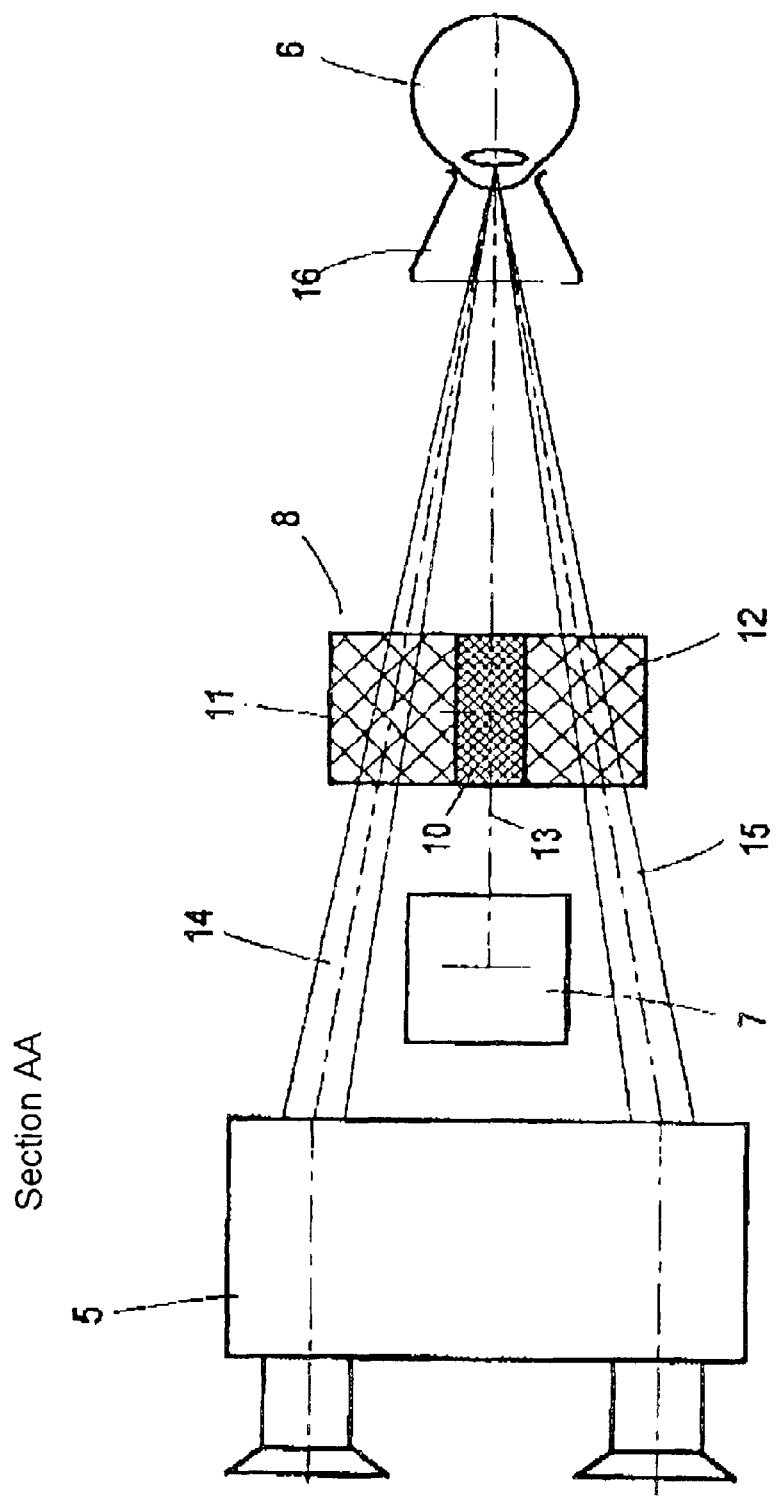

ARRANGEMENT FOR LASER COAGULATION

BACKGROUND OF THE INVENTION a) Field of the Invention

The invention is directed to an arrangement for laser coagulation at the ocular fundus with at least one illumination light source for an illumination beam path, with a laser arrangement for generating a sighting beam path and a treatment or therapy beam path, wherein the sighting radiation and therapy radiation have different wavelengths, with observation optics for visual observation of the ocular fundus, for selecting the coagulation site and/or for monitoring the results of coagulation, and with a protective mechanism which prevents the laser radiation from penetrating into the eye of the person administering treatment. An individual laser with a plurality of different laser light wavelengths and the combination of a plurality of lasers with different wavelengths and corresponding driving circuits are also possible as a laser arrangement for radiating the sighting radiation and therapy radiation.

b) Description of the Related Art

In laser coagulation on the human eye, the desired therapeutic effect is achieved by thermal alteration of tissue in selected areas of the ocular fundus. For this purpose, energy in the form of laser light pulses is introduced into the tissue. With pulse lengths of 20 to 1000 milliseconds and outputs of around 200 mW, the radiated energy is absorbed, so that the surrounding tissue is heated locally. The success of the coagulation can be identified by a whitish color (necrosis) at the coagulation site and can be observed and monitored by the treating person through visual inspection of the ocular fundus, e.g., by means of a slit lamp. The end of the treatment is determined by observation based on subjective appraisal.

Since the observation light as well as the sighting radiation and therapy radiation penetrate into the patient's eye and are reflected therein during a treatment of this kind, the eye of the treating person is also always at risk and it is accordingly necessary to protect the eye of the treating person from reflected therapy radiation.

According to known prior art, in order to prevent injuries resulting from the reflected therapy radiation, separate component groups or subassemblies are used for the reflection of the therapy radiation into the observation beam path and the optical coupling out of the therapy radiation from the radiation reflected by the ocular fundus before this radiation reaches the eye of the treating physician. In particular, the use of eye protection filters which are swiveled into and out of the radiation coming from the ocular fundus by means of mechanical devices is known.

Since known devices comprise a plurality of component groups and/or must be composed of a number of structural component parts, they have the disadvantage that assembly of such arrangements is complicated and requires extensive space, which undermines the effort toward more economical and also miniaturized medical instruments. In addition, an increasing number of parts in the protective devices require swiveling mechanisms which are more complicated and therefore more susceptible to malfunction. In the event of failure of the swiveling mechanisms, the eye protection filter cannot be swiveled into the beam path and the dangerous therapy radiation can reach the eye of the treating physician.

OBJECT AND SUMMARY OF THE INVENTION

Consequently, it is the primary object of the invention to further develop an arrangement for laser coagulation of the type described above so as to further increase the safety of the treating person.

The object of the invention is met in that an optical element which is arranged in the sighting and therapy beam path is provided as a protective device, wherein this optical element has a plurality of optically active areas whose optical characteristics differ from one another. In this way, an uncomplicated construction of the device which is characterized by an extremely high degree of safety for the treating person is achieved.

It can be provided in an advantageous manner that the optical element has an optically active central area and at least one optically active edge area, wherein the central area is opaque to the sighting radiation and therapy radiation, but reflects this radiation, while the at least one edge area is opaque to the therapy radiation but transparent to the sighting radiation, and wherein the optical element is positioned in such a way that the sighting radiation and therapy radiation coming from the laser impinges on the central area and is deflected by the latter onto the ocular fundus, and the at least one edge area is arranged before the observation optics in the beam path of the sighting radiation and therapy radiation reflected by the patient's eye.

Due to this configuration of the optical element and its arrangement in the beam path, it is achieved, first, that the radiation coming from the laser arrangement, i.e., the sighting radiation as well as the therapy radiation, is reflected by the optical element onto the ocular fundus and, second, that the therapy radiation cannot reach the eye of the treating physician either via the edge area or via the central area because the central area and the edge area of the optical element are both constructed so as to be opaque to the therapy radiation. This eliminates danger in every case.

The edge area is transparent only to the sighting radiation which is reflected by the eye and which, after passing through the edge area, strikes the observation optics and is perceived by the treating physician in a harmless manner and can be utilized to target the coagulation site selected for treatment.

In a further preferred arrangement of the optical element, the central area and the at least one edge area are constructed so as to be transparent to the illumination radiation, and the optical element is arranged in such a way that the illumination radiation reflected by the ocular fundus passes through the optical element to the observation optics. Accordingly, the illumination radiation reflected by the ocular fundus can be used for observing and diagnosing the retina. Depending on the results of the diagnosis, the laser arrangement is switched on for the purpose of initially coupling in the sighting radiation and then, in order to perform the treatment, coupling in the therapy radiation.

The illumination radiation can be mixed in or faded in, for example, by a reflecting structural component part arranged in the beam path between the optical element and the observation optics. In order to achieve this coupling in, the central area is advantageously constructed so as to be dichroitic in that it is transparent to the illumination radiation in the direction of the ocular fundus, but reflects, and is opaque to, the sighting radiation and therapy radiation in the opposite direction, while the at least one edge area is transparent to the illumination light reflected in the patient's eye as well as to the sighting radiation in the direction of the observation optics.

This arrangement is also useful for an uncomplicated and accordingly less cumbersome construction of the arrangement according to the invention for laser coagulation while having an extremely small overall size.

A very preferable construction of the invention in which a stereo microscope is provided as observation optics is characterized in that the dichroitic central area of the optical element is oriented approximately centric to the axis of symmetry of the observation radiation, sighting radiation and therapy radiation reflected by the ocular fundus, and the optical element has two edge areas, each of which is arranged, respectively, in one of the two observation beam paths of the stereo microscope. Accordingly, by means of the arrangement according to the invention, the advantages of stereoscopic viewing can be utilized to their full extent in diagnosing the ocular fundus without endangering the eyes of the treating physician.

Further, it is possible to arrange the optical element such that its position and orientation with respect to the illumination beam path and/or with respect to the sighting radiation and therapy radiation is unchangeable, so that it is not necessary to swivel it in and out of the beam path.

Therefore, the use of drives and swiveling mechanisms is avoided and endangerment of the treating person due to a failure of such arrangements is accordingly prevented. The optical element is fixedly installed in the device; it is not necessary to change its position or orientation relative to the beam paths either before, during or after the laser treatment. Accordingly, the therapy radiation is compulsorily coupled out of the observation beam path before the observation radiation can reach the eye of the operator. Further, no additional manipulation is required for swiveling in and out. In addition to the advantages of increased safety and improved handling, the elimination of moving parts at the same time also reduces mechanical wear and prolongs the useful life of such arrangements. Another substantial advantage consists in the prevention of involuntary eye movements of the patient which tend to be caused by unexpected or unexplained movements or noises during the treatment.

In a preferred arrangement, Nd-YAG lasers with frequency doubling are provided in the laser arrangement with therapy radiation in the wavelength range of 532 nm (green) and with sighting radiation in the wavelength range of 630 nm to 680 nm (red). This ensures the use of lasers which have already proven successful when used for coagulation of the ocular fundus and which are commercially obtainable as component groups or modules.

The optical element can be manufactured, for example, from glass with a coating in the central area which is generally transparent to the wavelength range of visible light, but has a narrow band for wavelength ranges of 532 nm and around 680 nm and accordingly reflects the sighting radiation and therapy radiation, while the edge areas are provided with a coating which has a narrow-band and is opaque to the therapy radiation.

Further, the slit projector of a slit lamp can advantageously be provided as the illumination light source. This makes it possible to observe and diagnose the ocular fundus in a conventional manner.

The invention will be explained more fully hereinafter with reference to an embodiment example.

BRIEF DESCRIPTION OF THE DRAWINGS

Shown in the drawings are:

FIG. 2 a view of the beam configuration in a section AA from FIG. 1.

DESCRIPTION OF THE PREFERRED EMBODIMENTS

Figure 1:
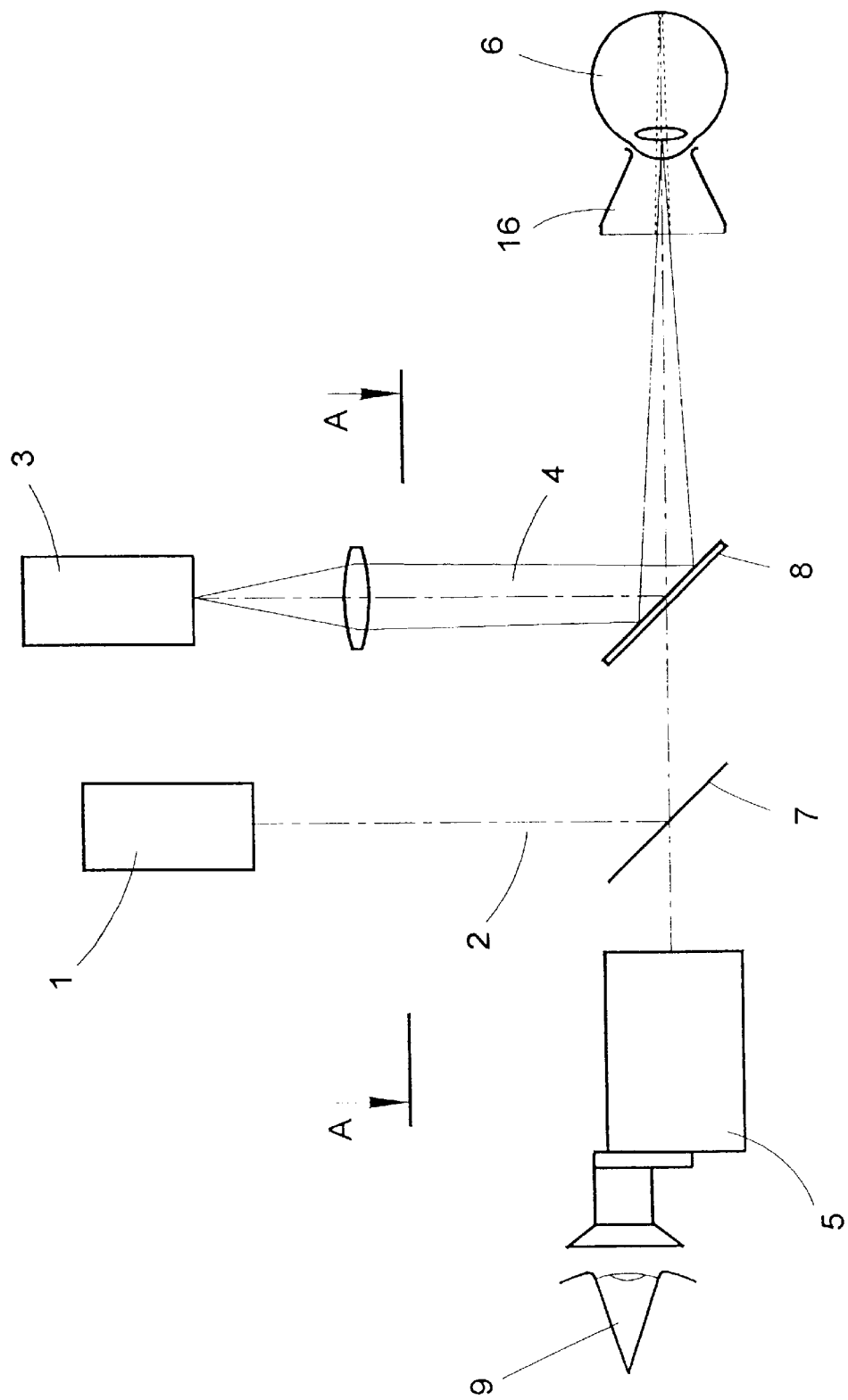
FIG. 1 the basic construction of the arrangement and the insertion of the optical element in the beam path.

FIG. 1 shows an arrangement for laser coagulation at the ocular fundus with an illumination light source 1 for an illumination beam path 2, with a laser arrangement 3 for generating sighting radiation and therapy radiation 4, wherein the sighting radiation and therapy radiation have different wavelengths, with a stereo microscope 5 for visual observation of the ocular fundus of the patient's eye 6. The stereo microscope 5 also makes it possible at the same time to select the coagulation site and/or to monitor the results of coagulation. Two laser light sources (not shown individually) are provided in the laser arrangement, a first laser light source radiating the sighting radiation with a wavelength of 630 nm and a second laser light source radiating the therapy radiation with a wavelength of 532 nm; both lasers can be driven separately via a driving circuit (not shown).

The coupling in of the illumination beam path 2 and its deflection in the direction of the patient's eye 6 is carried out by a reflecting structural component part 7 which is arranged between the stereo microscope 5 and an optical element 8 and which serves to couple in the sighting radiation and therapy radiation 4 and deflect it in the direction of the patient's eye 6.

In order to prevent injury to the eye 9 of the treating person by the therapy radiation reflected by the fundus of the patient's eye 6, but in order at the same time to enable observation of the ocular fundus of the patient's eye 6 by means of the illumination light and to enable selection and sighting of a coagulation site by means of the sighting radiation, the optical element 8 has a plurality of optically active areas whose optical characteristics differ from one another.

In section AA from FIG. 1, shown in FIG. 2, these optically active areas are shown symbolically. A central area 10 is oriented roughly centric to the axis of symmetry 13 of the beam reflected from the fundus of the patient's eye 6. Aside from the central area 10, the optical element 8 also has two edge areas 11 and 12, each of which is arranged in one of the observation beam paths 14 and 15 of the stereo microscope 5. Observation is carried out, for example, by means of a Goldmann fundus contact lens 16 which approximately compensates for the refractive power of the cornea and optically shifts the fundus plane into the anterior section of the eye, for example, to the front surface of the lens.

The central area 10 is opaque to, but highly reflective of, the sighting radiation and therapy radiation 4. The two edge areas 11 and 12 are opaque to the therapy radiation, but transparent to the illumination radiation and sighting radiation.

The arrangement is operated such that the illumination light source 1 is first switched on for diagnosing or observing the fundus of the patient's eye 6. As was already shown with reference to FIG. 1, the illumination beam 2 proceeding from the illumination light source 1 is deflected by the reflecting structural component part 7 and is directed to the fundus of the patient's eye 6 through the central area 10 of the optical element 8 which is transparent to the wavelength of the illumination light (FIG. 1). The illumination light reflected by the ocular fundus reaches the eyepiece of the stereo microscope 5 via the two observation beam paths 14 and 15. Since the edge areas 11 and 12 are made transparent to the wavelength of the illumination light, the ocular fundus can be seen in the stereo microscope 5.

In order to enable the sighting of a target area at the fundus of the patient's eye 6 as well as the coagulation of selected portions of tissue of the ocular fundus by means of the same arrangement without endangering the eye 9 of the treating person by the therapy radiation reflected from the ocular fundus, the edge areas of the optical element 8 are formed so as to be opaque to the therapy radiation. Therefore, the edge areas 11 and 12 act as eye protection filters for the treating person and offer a high degree of safety.

The edge areas 11 and 12 are constructed so as to be transparent to the sighting radiation as well as to the illumination radiation 2, so that it is possible for the treating physician after switching on the laser arrangement 3 to operate this laser arrangement 3 initially with the sighting radiation which is radiated, e.g., in the wavelength of 630 nm and at a harmless output, e.g., of 1 mW.

After selecting and sighting the coagulation site, the laser arrangement can be switched to the therapy radiation operating mode with the wavelength of 532 nm and the coagulation can be carried out without requiring additional manipulation for safety measures.

The eye protection filter formed by the edge areas 11 and 12 enables sighting and coagulation as well as observation by means of the illumination light without risk as described above.

While the foregoing description and drawings represent the preferred embodiments of the present invention, it will be obvious to those skilled in the art that various changes and modifications may be made therein without departing from the true spirit and scope of the present invention.

REFERENCE NUMBERS 1 illumination light source
2 illumination beam path
3 laser arrangement
4 sighting and therapy beam path
4 stereo microscope
5 patient's eye
6 reflecting structural component part
7 optical element
7 eye
8 central area
11, 12 edge areas
13 axis of symmetry
14, 15 observation beam path
16 fundus contact lens

What is claimed is:

1. An arrangement for laser coagulation at the ocular fundus comprising:
   at least one illumination light source for an illumination beam path;
   a laser arrangement for generating a sighting and therapy beam path, wherein the sighting radiation and therapy radiation have different wavelengths;
   observation optics for visual observation of the ocular fundus, for selecting the coagulation site and for monitoring the results of coagulation;
   a protective mechanism which prevents the laser radiation from penetrating into the eye of the person administering treatment; and
   an optical element which is arranged in the sighting and therapy beam path being provided as a protective device, wherein this optical element has a plurality of optically active areas whose optical characteristics differ from one another.

2. The arrangement according to claim 1, wherein the optical element has an optically active central area and at least one optically active edge area, wherein the central area is opaque to the sighting and therapy radiation, but reflects this radiation, while the at least one edge area is opaque to the therapy radiation but transparent to the sighting radiation, and wherein the optical element is positioned in such a way that the sighting and therapy radiation coming from the laser impinges on the central area and is deflected by the latter into the patient's eye, and the at least one edge area is arranged before the observation optics in the beam path of the sighting and therapy radiation reflected by the patient's eye.

3. The arrangement according to claim 2, wherein the central area and the at least one edge area are constructed so as to be transparent to the illumination radiation, and the optical element is arranged in such a way that the illumination radiation reflected by the ocular fundus passes through the optical element to the observation optics.

4. The arrangement for laser coagulation according to claim 1, in which a stereo microscope is provided as observation optics, and wherein the central area of the optical element is oriented approximately centric to the axis of symmetry of the observation radiation and sighting radiation and therapy radiation reflected by the ocular fundus, and the optical element has two edge areas, each of which it arranged, respectively, in one of the two observation beam paths of the stereo microscope.

5. The arrangement according to claim 1, wherein the optical element is unchangeable with respect to its position and orientation relative to the illumination beam path and relative to the sighting and therapy radiation.

6. The arrangement for laser coagulation according claim 1, wherein a Nd-YAG laser with frequency doubling is provided as laser with a therapy radiation in the wavelength range of 532 nm and with a sighting radiation in the wavelength range of 630 nm to 680 nm.

7. The arrangement for laser coagulation according to claim 1, wherein a slit projector of a slit lamp is provided as the illumination light source.

8. An arrangement for laser coagulation at the ocular fundus with at least one illumination light source (1) for an illumination beam path (2), with a laser arrangement (3) for generating a sighting and therapy beam path (4), wherein the sighting radiation and therapy radiation have different wavelengths, with observation optics for visual observation of the ocular fundus, for selecting the coagulation site and for monitoring the results of coagulation, and including a protective device which prevents the laser radiation from penetrating into the eye of the person administering treatment, wherein optical element (8) which is arranged in the sighting and therapy beam path (4) is provided as a protective device, wherein this optical element (8) has a central area (10) which is constructed so as to be opaque to the sighting and therapy radiation but reflects this radiation, and has at least one edge area (11, 12) which is opaque to the therapy radiation but transparent to the sighting radiation, and wherein the optical element (8) is positioned in such a way that the sighting and therapy radiation coming from the laser impinges on the central area (IO) and is deflected by the latter into the patient's eye (6), and the at least one edge area (11, 12) is arranged before the observation optics in the beam path of the sighting and therapy radiation reflected by the patient's eye (6).

* * * * *